United States Patent
Xu et al.

(10) Patent No.: US 7,067,432 B2
(45) Date of Patent: Jun. 27, 2006

(54) METHODOLOGY FOR IN-SITU AND REAL-TIME CHAMBER CONDITION MONITORING AND PROCESS RECOVERY DURING PLASMA PROCESSING

(75) Inventors: Songlin Xu, Fremont, CA (US); Thorsten Lill, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 140 days.

(21) Appl. No.: 10/608,670

(22) Filed: Jun. 26, 2003

(65) Prior Publication Data

US 2004/0263827 A1    Dec. 30, 2004

(51) Int. Cl.
*H01L 21/302* (2006.01)

(52) U.S. Cl. ............... 438/710; 438/9; 438/706; 438/712; 134/1.1

(58) Field of Classification Search ............... 438/7, 438/9, 706, 710, 712, 714, 717, 725; 216/59, 216/60; 134/1.1, 1.2
See application file for complete search history.

(56) References Cited

U.S. PATENT DOCUMENTS

| | | | |
|---|---|---|---|
| 5,756,400 A | | 5/1998 | Ye et al. |
| 5,788,799 A | | 8/1998 | Steger et al. |
| 5,879,575 A | | 3/1999 | Tepman et al. |
| 6,124,927 A | * | 9/2000 | Zhong et al. ............ 356/311 |
| 6,143,144 A | * | 11/2000 | Golovato et al. ....... 204/192.33 |
| 6,274,500 B1 | | 8/2001 | Xuechun et al. |
| 6,379,575 B1 | | 4/2002 | Yin et al. |
| 6,797,634 B1 | * | 9/2004 | Suzuki ...................... 438/706 |

OTHER PUBLICATIONS

Songlin Xu et al., "Wall-dependent etching characteristics of organic antireflection coating in $O_2$+halogen/hydrogen halide plasma", J. Vac Sci. Technol. A 19(6), Nov./Dec. 2001.
Songin Xu et al., "Gate Oxide Integrity Issue Cause by Wall-Related Process Drivt in Plasma Etching", 2002 7th International Symposium on Plasma-and Process-Induced Damage Jun. 6-7, Maui HI, USA.
Songlin Xu et al., "Characteristics and mechanism of etch process sensitivity to chamber surface condition", J. Vac. Sci. Technol. B19(1), Jan./Feb. 2001.

* cited by examiner

*Primary Examiner*—Lan Vinh
(74) *Attorney, Agent, or Firm*—Patterson & Sheridan LLP

(57) ABSTRACT

A new methodology of monitoring process drift and chamber seasoning is presented based on the discovery of the strong correlation between chamber surface condition and free radical density in a plasma. Lower free radical density indicates either there is a significant process drift in the case of production wafer etching or that the chamber needs more seasoning before resuming production wafer etching. Free radical density in the plasma is monitored through measuring the emission intensities of free radicals in the plasma by an optical spectrometer. A timely detection of the extent of process drift and chamber seasoning can help to minimize the chamber downtime and improve its throughput significantly. Such method can also be implemented in existing production wafer etching or chamber seasoning practices in an in-situ, real-time, and non-intrusive manner.

14 Claims, 4 Drawing Sheets

METHODOLOGY FOR IN-SITU AND REAL-TIME CHAMBER CONDITION MONITORING AND PROCESS RECOVERY DURING PLASMA PROCESSING

The present application relates to semiconductor processing technology and particularly to a method of in-situ process monitoring, effective chamber seasoning and process recovery during plasma processing.

BACKGROUND OF THE INVENTION

Semiconductor fabrication includes a series of processes that produce electrical circuits in a semiconductor, e.g., a silicon wafer, in accordance with a circuit design. These processes are carried out in a series of chambers. Successful operation of a modern semiconductor fabrication facility requires a steady stream of wafers to be moved from one chamber to another in the course of forming electrical circuits in the wafer.

One important process is plasma etching, which is a process of transferring a pattern in a layer of mask material into another layer under the mask, such as a layer of conductive or dielectric material, by removing the layered material from the wafer surface. Such process inevitably generates different kinds of etch by-products, such as silicon oxide and organic polymer, depending on the layered material and the etch chemistry. Some of the by-products deposit onto interior surfaces of the chamber in which the plasma etching process is performed.

The continuing build-up of by-products on interior surfaces, such as the chamber wall, presents two challenges to semiconductor fabrication. First, the structure of the accumulated by-products is not stable. Thus, by-products tend to peel off the chamber wall generating particles and flakes that can fall upon the wafer surface, causing product defects, such as a short circuit between two conductive lines or a discontinuity where the upper layer cannot cover the debris. Second, the by-products remaining on the chamber wall react with the plasma and deleteriously affect the etch performance, a phenomenon that is also referred to as "process drift".

To mitigate the impact of etch by-products, chamber cleaning is required to periodically remove the deposition from the chamber wall. To do this, the chamber is taken out of production, and a cleaning plasma, such as a $CF_4+O_2$ plasma for cleaning silicon oxide deposited during silicon etching, is introduced into the chamber. This plasma reacts with the deposition and the products of this reaction are pumped out of the chamber. After such chamber cleaning, however, it has been observed that a clean chamber wall makes the chamber unsuitable for immediate production wafer etching. This is referred to as "first wafer effect". Chamber seasoning is a procedure of etching a series of blank silicon wafers to restore a chamber wall condition that is suitable for production wafer etching. After chamber seasoning, a thin layer of silicon oxide covers the chamber wall. The chamber is then returned to production wafer etching until the next round of chamber cleaning and seasoning becomes necessary.

Some key factors for evaluating etch performance include etch rate, etch selectivity, and undercut. Etch rate refers to the rate at which a layered material is removed from a wafer surface. Etch selectivity is defined as the ratio of etch rates between two layers under the same conditions. Undercut is a measure of the lateral extent of the etch under the mask. The smaller the undercut, the better the etch profile control.

A critical issue in process monitoring and chamber seasoning is how to identify the process drift and when to stop seasoning to return to production wafer etching. The conventional practice in the art is to measure the change of etch rate by periodically loading monitor wafers into the chamber. Such practice, however, causes too many interruptions to the production or seasoning and lowers the chamber throughput. In addition, such approach is empirically based and tends to stop production prematurely for cleaning or result in over-seasoning.

Therefore, it is highly desirable to develop a method of process monitoring and chamber seasoning that does not rely on measuring the etch rate and thereby avoids interruptions to production or seasoning. It is also preferred that such method monitors the chamber wall condition in a manner so as to provide real-time, accurate information about process drift and chamber seasoning.

SUMMARY

The present invention provides a novel methodology for in-situ process monitoring, effective chamber seasoning and process recovery in a plasma etching process. The present invention is based on the discovery that a plasma property, particularly free radical density, has a strong correlation with the by-products deposited on the chamber wall, and that a change in free radical density is related to change in etch rate.

More specifically, the present invention measures the emission intensities of different free radicals and an inert gas molecule, such as Ar, in a plasma using optical actinometry. If the density of the inert gas molecule is controlled to be constant, the ratio of emission intensities between a free radical and the inert gas molecule is an accurate measure of the density of the free radical. This ratio is used in the present invention to indicate the chamber wall condition.

In a first aspect of the present invention, a probing gas is introduced into the chamber and struck into a probing plasma in the absence of any wafer to be etched. The probing gas includes a source of free radicals such as HBr, $Cl_2$, $O_2$, or $CF_4$ and a certain amount of an inert gas such as Ar or Xe, preferably Ar. The free radical density in the probing plasma reflects the extent of etch by-products deposited on the chamber wall and can be used to determine if the chamber is in stable condition during production or if chamber seasoning is complete.

In a second aspect of the present invention, a certain amount of inert gas such as Ar or Xe is introduced into the chamber with a seasoning plasma during chamber seasoning. The free radical density in the seasoning plasma is measured in an in-situ, real-time, and non-intrusive manner to reflect the extent of chamber wall deposition and can be used to determine if the chamber seasoning is complete or not.

In a third aspect of the present invention, a certain amount of inert gas such as Ar or Xe is introduced into the chamber with production plasma during production wafer etching. The free radical density of the production plasma is measured in an in-situ, real-time and non-intrusive manner to indicate the extent of process drift and can be used to determine if the production wafer etching should be stopped to allow chamber cleaning.

BRIEF DESCRIPTION OF THE DRAWINGS

Additional objects and features of the invention will be more readily apparent from the following detailed description and appended claims when taken in conjunction with the drawings, in which:

DETAILED DESCRIPTION

The etching processes of the present invention can be performed in a plasma reactor, such as an Applied Materials De-coupled Plasma Source (DPS) silicon etch chamber.

Figure 1:
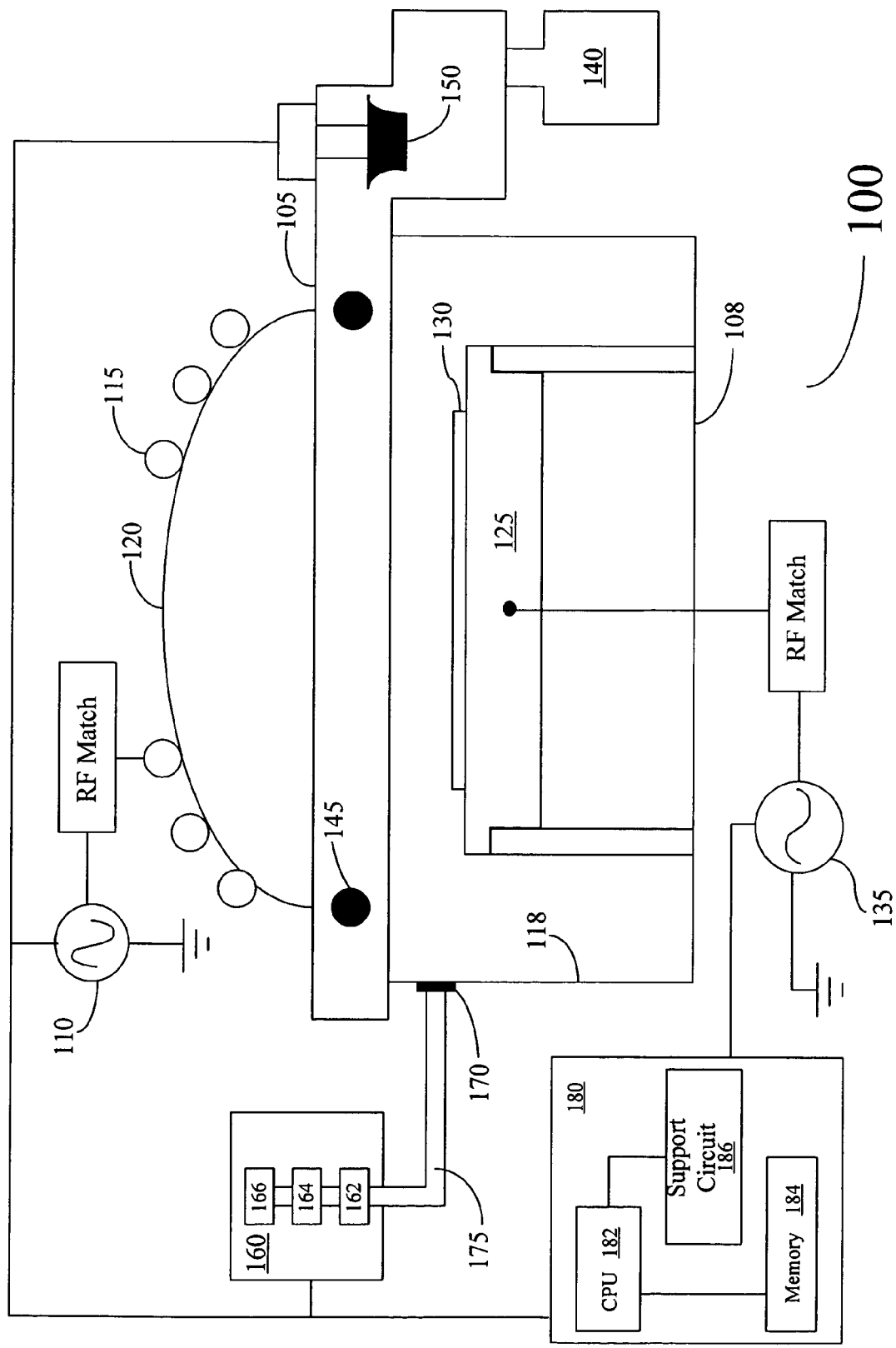
FIG. 1 is a schematic view of an inductively coupled plasma reactor according to one embodiment of the present invention.

FIG. 1 provides a schematic view of such a reactor. Plasma reactor 100 comprises an upper chamber body 105 and a lower chamber body 108. On top of the upper chamber body is a dielectric dome 120. A chamber wall 118 encloses the lower chamber body. The dome material is alumina and the chamber wall 118 is anodized aluminum. The dome and chamber wall are maintained at a constant temperature (80° C. for the dome and 65° C. for the chamber wall).

A high-density plasma is generated by applying a Radio Frequency (RF) power source 110 of 12.56 MHz to an inductive coil 115 on dielectric dome 120, which is set on top of the upper chamber body 105. A cathode 125 equipped with an electrostatic chuck (not shown) holds a semiconductor wafer 130, which is also thermally controlled during etching using helium backside cooling. A separate RF bias power source 135 of 13.56 MHz is applied to the cathode to control ion bombardment energy to the wafer. The chamber is evacuated by a 2000 l/s turbomolecular pump 140 backed by a dry mechanical pump (not shown).

Process gases are introduced through four gas distribution rings 145 on the chamber wall with controlled flow rates. Chamber pressure is maintained at a designated value with a throttle valve 150. An optical spectrometer 160 including a prism 162, a monochromator 164, and a photodiode array (PDA) detector 166, is used to record the optical emission spectrum. The optical signal is collected from the endpoint view window 170 of the chamber and fed into the spectrometer through a multi-strand optical fiber 175.

A control system 180 comprising a CPU 182, a memory 184, and support circuits 186 for the CPU 182 controls the various components of the plasma reactor 100. A software routine or a series of program instructions stored in the memory 184, when executed by the CPU 182, causes the reactor 100 to perform the processes of the present invention.

Depending on the etch chemistry, the interaction between the etchant and the material on the wafer surface produces many kinds of etch by-products. Some of the by-products deposit onto the chamber wall. For example, polysilicon gate etching using $Cl_2$- or HBr-based plasma with some $O_2$ added generates silicon oxide, a common nonvolatile etch by-product. After a certain period of polysilicon gate etching, the chamber wall is covered with a thick layer of silicon oxide. Besides oxide deposition, organic polymer is another common deposition. Organic polymer is usually produced in the etch steps preceding the polysilicon gate etching, such as the opening of the mask or an anti-reflection coating using a fluorocarbon plasma.

The chamber wall deposition not only creates particulate contamination on the wafer surface, but also affects the density of neutral free radicals in the plasma. The reason is that the surface recombination rate of free radicals varies significantly depending on the chamber wall condition. The higher the surface recombination rate of free radicals, the lower the density of free radicals in the plasma. Free radicals react with wafer surface materials and turn them into some volatile by-products during etching, which are then pumped out of the chamber. Therefore, lower free radical density in the plasma indicates lower etch performance.

Figure 2:
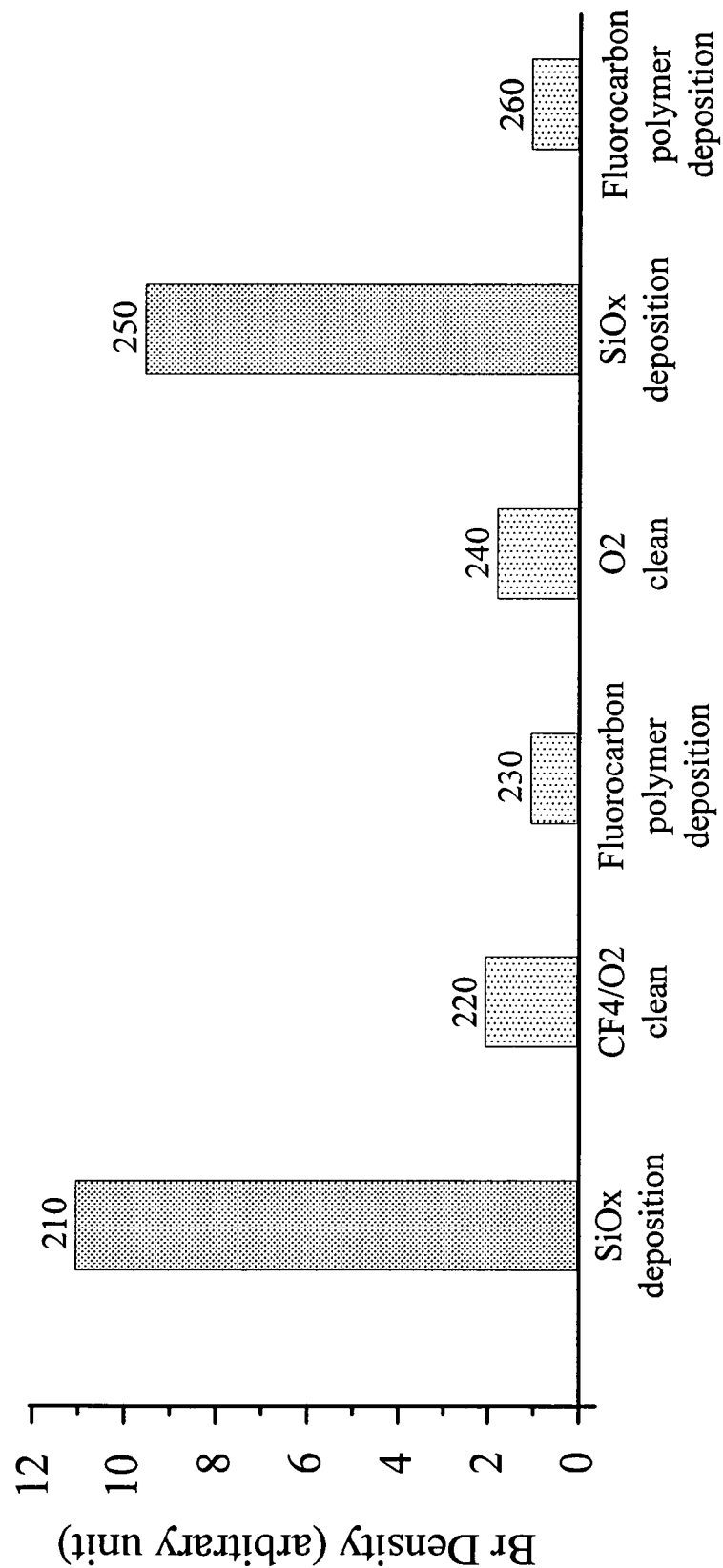
FIG. 2 depicts the variation of relative density of Br free radical in an HBr-based plasma with 7% Ar added after a series of chamber treatments.

FIG. 2 depicts the variation of relative Br free radical density of a HBr-based plasma with 7% Ar added in a plasma chamber under three typical chamber wall conditions, i.e., chamber wall covered with $SiO_x$ deposition, clean chamber wall, and chamber wall covered with fluorocarbon polymer deposition. This data demonstrates the correlation between the free radical density and the chamber wall condition.

Bar 210 indicates that when the chamber wall is coated with a thin layer of $SiO_x$ deposition, the relative density of Br free radical is about 11 units. Bar 220 indicates that the relative density of Br free radical drops to 2 units following a chamber cleaning using $CF_4/O_2$ plasma. Bar 230 indicates that the relative density of Br free radical further drops to 1 unit following a long period of etching an anti-reflection coating using fluorocarbon plasma. In the course of such etching, the chamber wall is coated with a thick layer of fluorocarbon polymer causing a significant process drift.

Bar 240 indicates that the relative density of Br free radical returns to 2 units following a second chamber cleaning using $O_2$ plasma. Bar 250 indicates the relative density of Br free radical rises to 10 units following a second chamber seasoning step. And bar 260 indicates that the relative density of Br free radical drops to 1 unit once again following a second round of an etching process that opens an anti-reflection coating using fluorocarbon plasma.

It is apparent from the foregoing that the relative density of the Br free radical is about a magnitude higher immediately after chamber seasoning than immediately after chamber cleaning or when there is a significant process drift. In addition, the Br density with a clean chamber wall is slightly higher than when the walls are covered with a fluorocarbon polymer. Since it is the chemical reaction between neutral free radicals in the $Cl_2$- or HBr-based plasma and the polysilicon that etches out unwanted materials from the wafer surface and creates the desired circuit pattern, the etch rate drops significantly when a clean chamber wall or a polymer coating reduces the free radical density.

Figure 3:
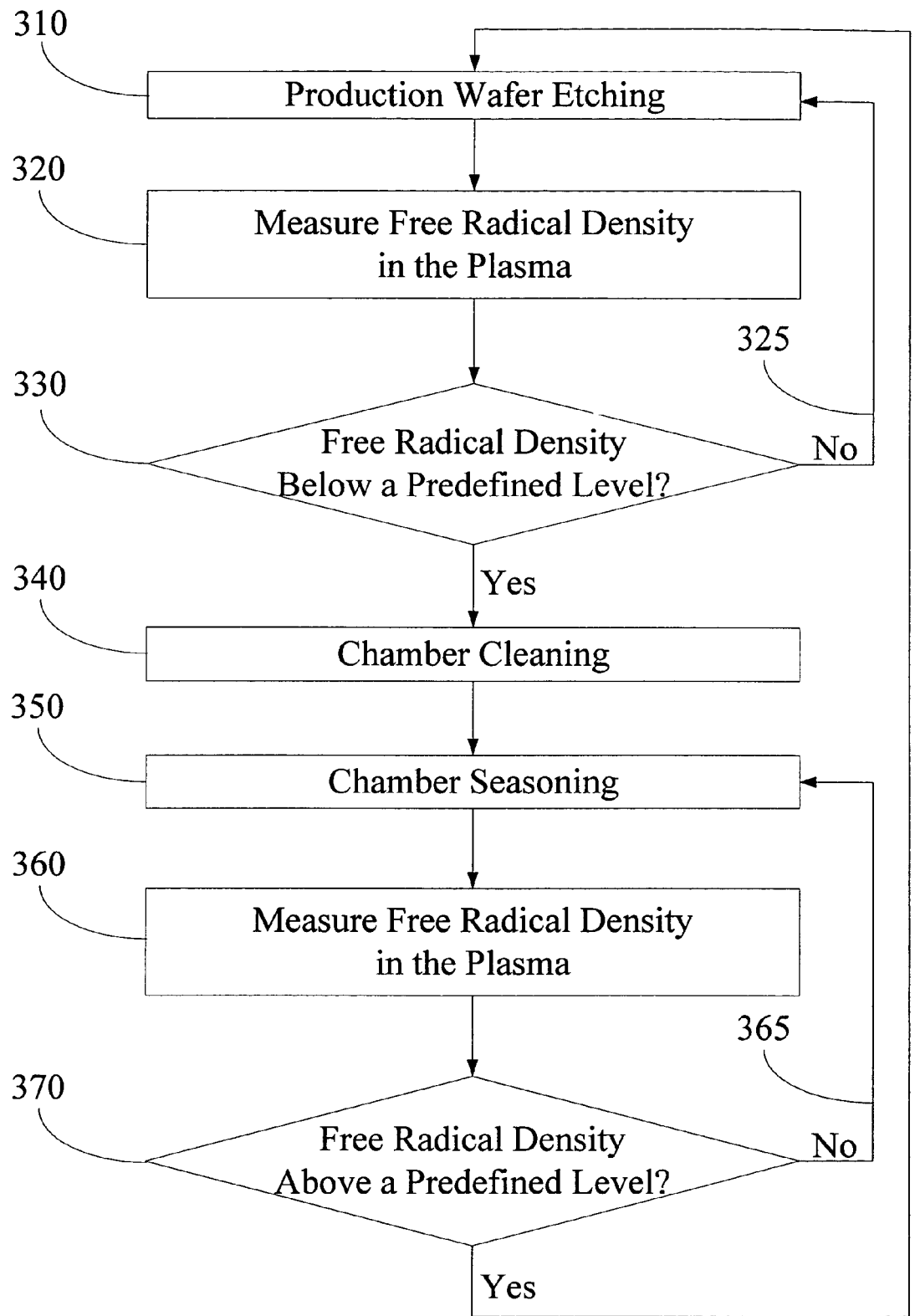
FIG. 3 is a flow chart illustrating the cycle of production wafer etching, chamber cleaning, and chamber seasoning according to one embodiment of the present invention.

The present invention provides a method of monitoring changes in free radical density in the chamber under different chamber wall conditions so as to determine the extent of process drift or chamber seasoning in a timely fashion. FIG. 3 is a flowchart depicting a typical sequence of steps performed by plasma reactor 100 according to one embodiment of the present invention. Step 310 represents the use of the chamber for production wafer etching. In this step, a series of wafers are successively loaded into the chamber, etched and removed. This process is conventional and does not require further description here.

Figure 4:
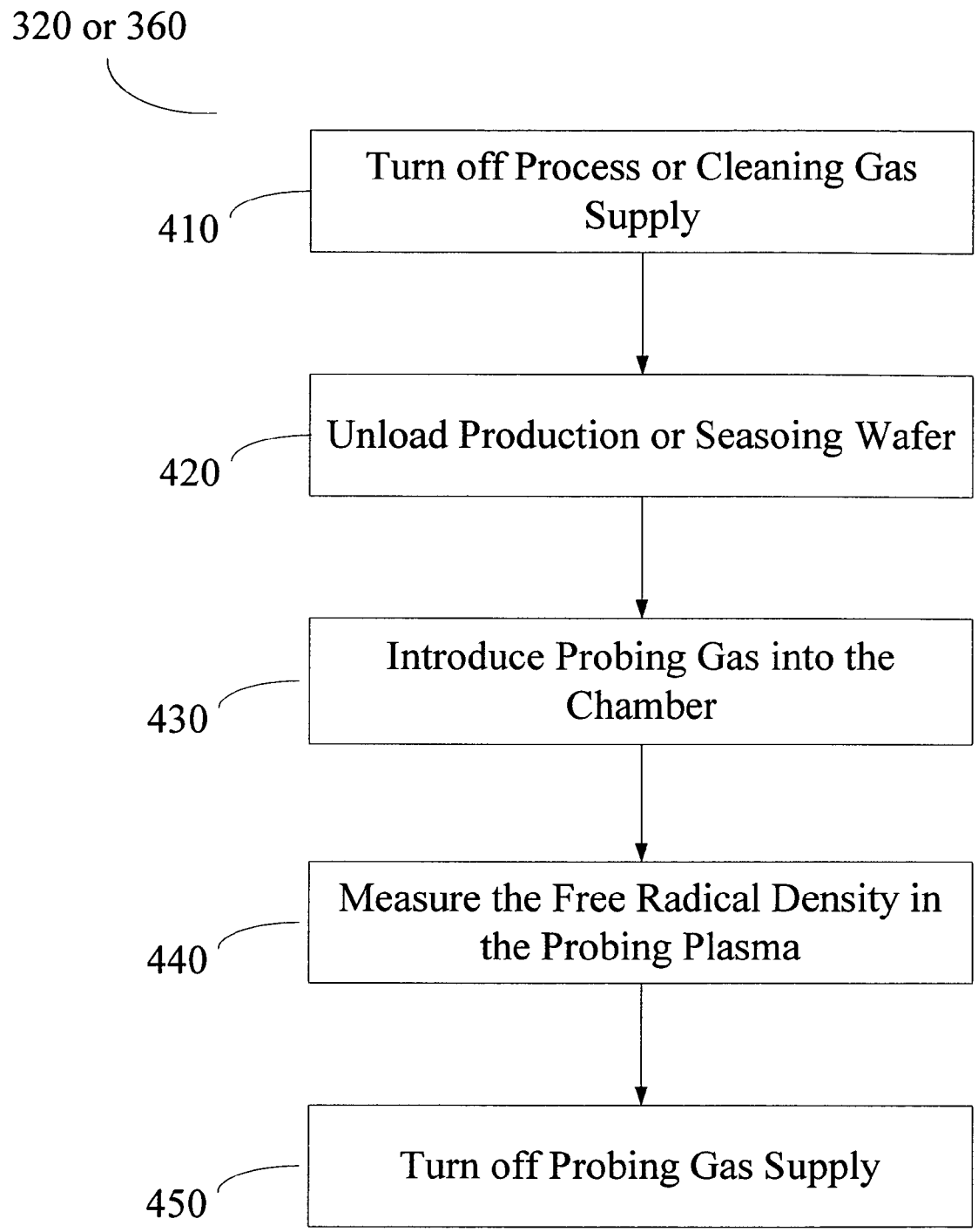
FIG. 4 is a flow chart illustrating the measurement of free radical density in a plasma according to one embodiment of the present invention.

Step 320 measures the free radical density in the plasma using the optical spectrometer 160 of FIG. 1. FIG. 4 provides more details about step 320. At step 410 the two RF power sources are turned off so as to stop the production of plasma. The process gas supply is then stopped and the remaining gases in the chamber are pumped out. At step 420 the production wafer is removed from the chamber. At step 430 a probing gas is introduced into the chamber and the RF power sources are turned on to strike the probing gas into plasma. Illustratively, the probing gas is HBr, $Cl_2$, $O_2$, or $CF_4$ with additional 5%–10% of Ar or Xe. In one example, the probing gas is HBr plus 7% Ar.

At step 440 the free radical density is measured in the probing plasma using the optical spectrometer 160. Optical spectrometer 160 analyzes the light emitted by excited atoms and molecules in the plasma. Photons passing through multi-strand optical fiber 175, prism 162, and monochromator 164, are detected by PDA detector 166. The properties of free radicals can be determined through analyzing these spectra. In particular, the emission intensities of Cl, Br, and O free radicals, $I_{free}$, are measured at 741.4 nm, 700.5 nm, and 844.6 nm, respectively, and the emission intensity of Ar molecule, $I_{Ar}$, is measured at 750.4 nm. The densities of Cl, Br, and O free radicals can be determined from the ratios of the emission intensities of Cl, Br and O with respect to the emission intensity of Ar $$\frac{I_{free}}{I_{Ar}}$$

To make this measurement, the optical spectrometer 160 samples the spectrum, for example, once per second for a few seconds. The data are then fed into computer control system 180 for further analysis. After system 180 determines an average free radical density of the probing plasma, the RF power sources are turned off at step 450, the probing gas supply is stopped and the chamber is back to production.

At step 330, the measured free radical density, which reflects the current chamber wall condition, is compared to a first predefined level. The first predefined level is that level at which the chamber wall condition is stable after a large number of wafers are etched. If the measured free radical density is above or within an acceptable range of the predefined level, the chamber can remain in production wafer etching; and, as indicated at 325, the process returns to step 310. Otherwise, the chamber is taken off production for chamber cleaning.

Any suitable procedure of removing the etch by-products from the chamber wall can be implemented at step 340. Different cleaning recipes have been developed to handle different etching by-products. This step does not require further description here.

The surface recombination rate of free radicals on anodized aluminum, i.e., a clean chamber wall, is more than ten times higher than that on a thin oxide deposit. Therefore, immediately after chamber cleaning, the free radical density is very low and the chamber condition is not suitable for production wafer etching. The chamber is restored to the normal chamber condition in chamber seasoning step 350 by etching a series of blank silicon wafers, e.g., 2–24 wafers, using seasoning plasma. Seasoning plasma is usually the same as production plasma. After chamber seasoning, the chamber wall is covered with a thin layer of silicon oxide and the free radical density in the plasma resumes normal levels.

In one embodiment of the present invention, the chamber seasoning step 350 is interrupted every one or two minutes as it approaches completion to measure the relative free radical density at step 360 so as to avoid chamber over seasoning. This measurement is performed as depicted in FIG. 4.

At step 370, the measured relative free radical density is compared to a second predefined level. The second predefined level is that level at which the chamber wall condition is deemed to be suitable for production wafer etching. This predefined level can be determined using known techniques. If the measured relative free radical density is still below the predefined level, chamber seasoning is resumed for another two minutes as indicated at 365. Otherwise, the chamber is ready to return production wafer etching as indicated at 375.

In a second embodiment of the present invention, the free radical density is measured while the chamber is seasoned by adding 5%–10% Ar or Xe directly into the seasoning plasma. In other words, steps 350, 360, and 370 are combined into a single step. Therefore, chamber seasoning can be monitored in a real-time and non-intrusive manner by measuring the emission intensity of free radicals in the seasoning plasma. This embodiment is more convenient, even though it is not as accurate as the first embodiment.

In a third embodiment of the present invention, relative free radical density is measured during production wafer etching 310 by adding 5%–10% Ar or Xe directly into the production plasma. In other words, steps 310, 320 and 330 are combined into a single step. Therefore, the chamber wall condition can be monitored in an in-situ, real-time and non-intrusive manner during production wafer etching by measuring the emission intensity of free radicals in the plasma. Again, this embodiment is more convenient over the use of a separate probing step for the same reason discussed above.

The foregoing description, for purposes of explanation, used specific nomenclature to provide a thorough understanding of the invention. However, it will be apparent to one skilled in the art that the specific details are not required in order to practice the invention. The embodiments were chosen and described in order to best explain the principles of the invention and its practical applications, to thereby enable others skilled in the art to best utilize the invention and various embodiments with various modifications as are suited to the particular use contemplated. Thus, the foregoing disclosure is not intended to be exhaustive or to limit the invention to the precise forms disclosed. Many modifications and variations are possible in view of the above teachings.

It is intended that the scope of the invention be defined by the following claims and their equivalents.

What is claimed is:

1. A method for in-situ and real-time plasma chamber condition monitoring, comprising:
   inserting a non-production wafer into a plasma chamber;
   injecting a probing gas into the plasma chamber, the probing gas comprising a source of free radicals, the probing gas having including an inert gas comprising for 5–10 percent of the probing gas;
   striking the probing gas into a probing plasma;
   measuring a density of the free radicals in the probing plasma, wherein the density of the free radicals is defined as a ratio of emission intensities of the free radicals and the inert gas, and wherein the density of the free radicals is compared with a first predefined level;

determining whether to commence plasma processing of a production wafer on the basis of the measured density of the free radicals; and taking the plasma chamber out of production in response to a determination that the density of the free radicals is below the first predefined level.

2. The method of claim 1 wherein the free radicals in the probing plasma include at least one of Br, Cl, O or F.

3. The method of claim 1 wherein the probing plasma also includes at least one of Ar or Xe.

4. The method of claim 1, wherein the source further comprises at least one of $Br_2$, $Cl_2$, $O_2$, and $CF_4$.

5. The method of claim 1 wherein the density of the free radicals is compared with a second predefined level.

6. The method of claim 5 further comprising: processing the production wafer in response to a determination that the density of the free radicals is above the second predefined level.

7. A method for controlling a seasoning process in a plasma chamber comprising:
   injecting a seasoning gas into a plasma chamber, the seasoning gas comprising a source of free radicals, and wherein the seasoning gas includes an inert gas and at least one of Br, Cl, O or F, the inert gas accounting for 5–10 percent of the seasoning gas;
   striking the seasoning gas into a seasoning plasma;
   seasoning the processing chamber;
   measuring a density of the free radicals in the seasoning plasma, wherein the density of the free radicals is defined as a ratio of emission intensities of the free radicals and the inert gas and wherein the density of the free radicals is compared with a predefined level;
   determining when the plasma chamber is seasoned according to the measured density of the free radicals; and
   extinguishing the seasoning plasma when the density of the free radicals is above the predefined level.

8. The method of claim 7 wherein the free radicals in the seasoning plasma include at least one of Br, Cl, O or F.

9. The method of claim 7 wherein the inert gas comprises at least one of Ar or Xe.

10. The method of claim 7, wherein the source further comprises at least one of $Br_2$, $Cl_2$, $O_2$, and $CF_4$.

11. A method for detecting process drift in a plasma chamber comprising:
    injecting a process gas into a plasma chamber, the process gas comprising a source of free radicals and an inert gas, the inert as accounting for 5–10 percent of the process gas;
    striking the process gas into a process plasma, wherein the process plasma includes an inert gas;
    measuring a density of the free radicals in the process plasma, wherein the density of the free radicals is defined as the ratio of emission intensities of the free radicals and the inert gas;
    determining an extent of process drift according to the measured density of the free radicals, wherein the density of the free radicals is compared with a predefined level; and
    deeming the plasma chamber unsuitable for production when the density of the free radicals is below the predefined level.

12. The method of claim 11, wherein the source further comprises at least one of $Br_2$, $Cl_2$, $O_2$, and $CF_4$.

13. The method of claim 11, wherein the free radicals in the process plasma include at least one of Br, Cl, O or F.

14. The method of claim 13 wherein the process plasma also includes at least one of Ar or Xe.

* * * * *

UNITED STATES PATENT AND TRADEMARK OFFICE
CERTIFICATE OF CORRECTION

| | | |
|---|---|---|
| PATENT NO. | : 7,067,432 B2 | Page 1 of 1 |
| APPLICATION NO. | : 10/608670 | |
| DATED | : June 27, 2006 | |
| INVENTOR(S) | : Xu et al. | |

It is certified that error appears in the above-identified patent and that said Letters Patent is hereby corrected as shown below:

In column 8, line 13, in Claim 11, delete "as" and insert -- gas --, therefor.

Signed and Sealed this

Thirty-first Day of October, 2006

JON W. DUDAS
*Director of the United States Patent and Trademark Office*